(12) United States Patent
Chiba et al.

(10) Patent No.: US 8,016,770 B2
(45) Date of Patent: Sep. 13, 2011

(54) COGNITIVE FUNCTION TRAINING UNIT

(75) Inventors: Yu Chiba, Kiyose (JP); Shogo Fukushima, Moriguchi (JP); Shuji Murakami, Takaishi (JP); Satoru Inakagata, Nara (JP); Akira Yamaguchi, Tokorozawa (JP)

(73) Assignee: Panasonic Electric Works Co., Ltd., Kadoma-shi (JP)

( * ) Notice: Subject to any disclaimer, the term of this patent is extended or adjusted under 35 U.S.C. 154(b) by 0 days.

(21) Appl. No.: 11/596,988

(22) PCT Filed: May 25, 2005

(86) PCT No.: PCT/JP2005/009539
§ 371 (c)(1),
(2), (4) Date: Nov. 20, 2006

(87) PCT Pub. No.: WO2005/115299
PCT Pub. Date: Aug. 12, 2005

(65) Prior Publication Data
US 2008/0027352 A1    Jan. 31, 2008

(30) Foreign Application Priority Data
May 26, 2004 (JP) ................................ 2004-156839

(51) Int. Cl.
*A61B 13/00* (2006.01)
(52) U.S. Cl. .......................... 600/558; 351/209; 351/211
(58) Field of Classification Search .................. 600/558; 128/897; 351/209, 211
See application file for complete search history.

(56) References Cited

U.S. PATENT DOCUMENTS 4,755,041 A * 7/1988 Ishikawa et al. ............. 351/211
4,889,422 A * 12/1989 Pavlidis ....................... 351/210
5,137,345 A    8/1992 Waldorf et al.
(Continued)

FOREIGN PATENT DOCUMENTS
JP           6-70885           3/1994
(Continued)

OTHER PUBLICATIONS

Duric et al. "Integrating Perceptual and Cognitive Modeling for Adaptive and Intelligent Human-Computer Interaction". 2002 IEEE pp. 1272-1285.*

(Continued)

*Primary Examiner* — Max Hlndenburg
*Assistant Examiner* — Renee Danega
(74) *Attorney, Agent, or Firm* — Edwards Angell Palmer & Dodge LLP

(57) ABSTRACT

A cognitive function training unit including an eye-target showing unit for showing a movable eye-target on a display disposed in front of the subject's eye, an eye movement measuring unit for measuring a position and/or movement of the subject's eye, and a judgment unit for judging whether or not the subject can fixedly look at or follow the eye-target based on the position and/or the movement of the eye-target shown on the display and the position and/or the movement of the subject's eye measured by the eye movement measuring unit, and the eye-target showing unit shows the eye-target repeatedly while changing the position and/or the movement of the eye-target according to a judgment result of the judgment unit. Therefore, it is possible to show a suitable eye-target according to a symptom of a patient, whereby it is possible to conduct training efficiently.

10 Claims, 5 Drawing Sheets

U.S. PATENT DOCUMENTS

| | | | |
|---|---|---|---|
| 5,555,895 A | | 9/1996 | Ulmer et al. |
| 5,852,489 A | | 12/1998 | Chen |
| 6,228,038 B1 | * | 5/2001 | Claessens .................. 600/558 |
| 2004/0257528 A1 | * | 12/2004 | Miyake et al. ............. 351/203 |

FOREIGN PATENT DOCUMENTS

| | | | |
|---|---|---|---|
| JP | 6-55203 | | 7/1994 |
| JP | 8-257079 | | 10/1996 |
| JP | 2003-47636 | | 2/2003 |
| JP | 200347636 | * | 2/2003 |
| WO | WO-00/57772 | | 10/2000 |
| WO | WO-01/64005 | | 9/2001 |
| WO | WO/01/64005 | * | 10/2001 |

OTHER PUBLICATIONS

Kasten et al. "Programs for diagnosis and therapy of visual field deficits in vision rehabilitation". Spatial Vision 1997, pp. 499-503.*
European Search Report dated Feb. 27, 2009, issued in EP 05743762. 6.

* cited by examiner

COGNITIVE FUNCTION TRAINING UNIT

BACKGROUND OF THE INVENTION

1. Field of the Invention

The present invention relates to a cognitive function training unit for conducting training for a cognitive dysfunction.

2. Description of the Related Art

When a person suffers damage to one side of a cerebral hemisphere, a symptom that neglects an object on the opposite side of the damaged side, namely, a symptom of unilateral spatial neglect appears. In most cases, a patient of the unilateral spatial neglect neglects an object on the left side of his or her visual space, and he or she misses an object on the left side, or bumps into a wall on the left side.

Japanese published examined application 6-55203 discloses a device which judges presence or absence of a brain disease by movement of a subject's line of sight. As to a simple method for judging the unilateral spatial neglect, a paper test, such as reproduction or a bisecting test of a line, is widely done.

However, as to a training method for the cognitive dysfunction by a cerebral dysfunction, such as the unilateral spatial neglect, a firm method has not been established yet.

SUMMARY OF THE INVENTION

In view of the above problem, the object of the present invention is to provide a cognitive function training unit which can conduct training for the cognitive dysfunction efficiently.

The cognitive function training unit of the present invention comprises an eye-target showing means for showing a movable eye-target on a display disposed in front of the subject's eye, an eye movement measuring means for measuring a position and/or movement of the subject's eye, and a judgment means for judging whether the subject can fixedly look at or follow the eye-target based on the position and/or the movement of the eye-target shown on the display and the position and/or the movement of the subject's eye measured by the eye movement measuring means, and the eye-target showing means shows the eye-target repeatedly while changing the position and/or the movement of the eye-target according to a judgment result of the judgment means.

In order to conduct training for cognitive dysfunction, such as the unilateral spatial neglect, efficiently, it is thought that it is effective to grasp a symptom of a patient precisely and extend a space gradually that the patient can recognize normally.

Because the cognitive function training unit of the present invention judges whether or not a subject can fixedly look at or follow an eye-target by the judgment means and shows the eye-target repeatedly while changing the position and/or the movement of the eye-target according to the judgment result of the eye-target showing means, it is possible to show a suitable eye-target according to a symptom of a patient, whereby it is possible to conduct training efficiently.

Preferably, the eye-target showing means changes the position and/or the movement of the eye-target so that the subject can fixedly look at or follow the eye-target, when the judgment means judges that the subject can not fixedly look at or follow the eye-target. In this case, an eye-target that the subject can not fixedly look at or follow is not shown for a long time, so it is possible to show a more suitable eye-target according to the symptom of the patient.

Preferably, the eye-target showing means repeatedly shows an eye-target which appears on the left side of a screen of the display and then moves to the right side, and when the judgment means judges that the subject can not follow the eye-target, the eye-target showing means moves a position at which the eye-target appears on the screen to the right. As mentioned above, most of the patients of the unilateral spatial neglect tend to neglect an object on the left side. So, by showing the eye-target which moves from the left side of the subject to the right, repeatedly, and instructing the subject to move the eyepoint to the left side as quickly as possible so that he or she can follow the eye-target which appears on the left side early, it can be expected to gradually extend a space that the subject of the unilateral spatial neglect can recognize normally to the left side. Furthermore, by moving the position at which the eye-target appears on the screen to the right so that the subject can follow the eye-target when the subject can not follow the eye-target, it is possible to show a more suitable eye-target according to the symptom of the patient. When the subject can not follow the eye-target, a movement speed of the eye-target may be slowed.

As to a judgment method of the judgment means, the judgment means can judge that the subject can not fixedly look at or follow the eye-target when the position of the subject's eye measured by the eye movement measuring means goes beyond a predetermined variation range. Or, the judgment means may judge that the subject can not fixedly look at or follow the eye-target when an eye velocity of the subject measured by the eye movement measuring means goes beyond a predetermined variation range.

Preferably, the judgment means judges the severity of the subject according to a degree that the subject can not fixedly look at or follow the eye-target, and the eye-target showing means changes the position and/or the movement of the eye-target according to the severity. In this case, it is possible to show a more suitable eye-target according to the severity of a disability of the subject.

In the above case, the cognitive function training unit may have a judgment mode for judging the severity of the subject and a rehabilitation mode for training the cognitive function of the subject, and in the judgment mode, the eye-target showing means may show the eye-target in a predetermined test pattern and the judgment means may judge the severity of the subject according to the degree that the subject can not fixedly look at or follow the eye-target, and in the rehabilitation mode, the eye-target showing means may change the position and/or the movement of the eye-target according to the severity of the subject judged in the judgment mode.

Preferably, the eye-target showing means can show an eye target of a 3-dimensional image on the display. In this case, it becomes possible to show various eye-targets, for example, an eye-target that moves from a right back of the screen to a left front thereof, whereby it is possible to show a more suitable eye-target according to the symptom of the subject.

Preferably, the display, the eye-target showing means, the eye movement measuring means, and the judgment means are housed in one case, and the case is able to be mounted on a head of the subject. In this case, the subject can conduct training for the cognitive function easily just by wearing the cognitive function training unit on the head. Furthermore, even if the subject moves his or her head, it is possible to show the eye-target at an intended position precisely, whereby it is possible to conduct training more efficiently.

DETAILED DESCRIPTION OF EXEMPLARY EMBODIMENTS

Hereinafter, the present invention will be described in more detail with reference to the accompanying drawings.

Figure 1:
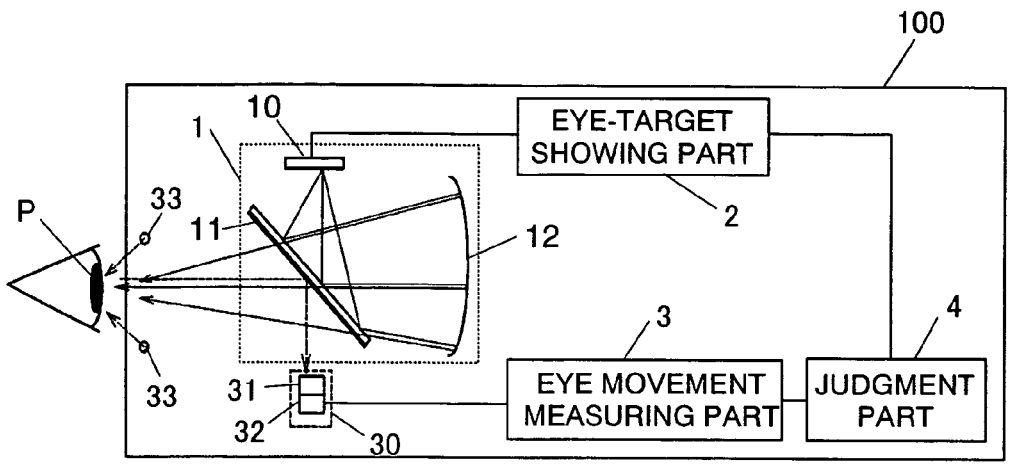
FIG. 1 is a view showing a constitution of a cognitive function training unit in accordance with a first embodiment of the present invention.
Figure 2:
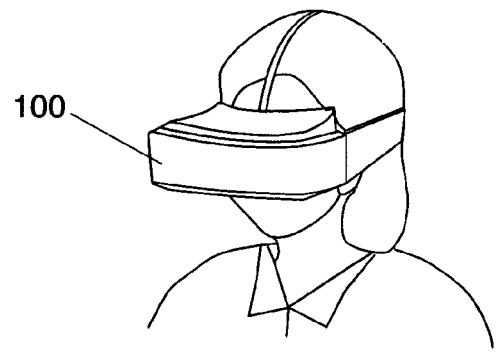
FIG. 2 is a view showing a condition where the cognitive function training unit was mounted on a subject's head.

FIG. 1 shows a constitution of a cognitive function training unit in accordance with a first embodiment of the present invention. The cognitive function training unit has a display unit 1 to be disposed in front of eyes of a subject, an eye-target showing part 2 for showing a movable eye-target on the display unit 1, an eye movement measuring part 3 which is connected to an imaging device 30 and measures a position and/or movement of the subject's eyes, and a judgment part 4 for judging whether the subject can fixedly look at or follow the eye-target by comparing the position and/or the movement of the eye-target shown on the display unit 1 with the position and/or the movement of the subject's eyes measured by the eye movement measuring part 3. The display unit 1, the eye-target showing part 2, the eye movement measuring part 3, the imaging device 30, and the judgment part 4 are housed in one case 100, and as shown in FIG. 2, when the cognitive function training unit is used, it is mounted on a head of the subject.

The display unit 1 comprises a liquid crystal display device 10, a half mirror 11, and a concave mirror 12. An image that the liquid crystal display device 10 shows is reflected by the half mirror 11 and the concave mirror 12, and is shown to the subject through the half mirror 11.

Figure 3:
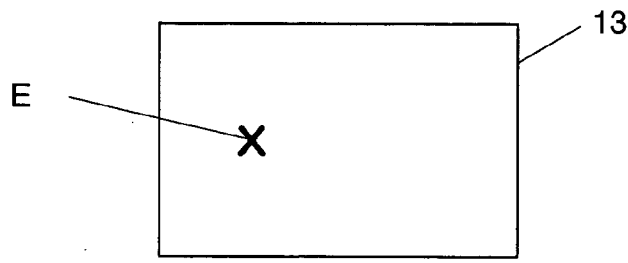
FIG. 3 is a view of one example of an eye-target to be shown to the subject in the cognitive function training unit.

The eye-target showing part 2, the eye movement measuring part 3, and the judgment part 4 are constituted by a microprocessor and so on. The eye-target showing part 2 shows, for example, an X-shaped eye-target E on a screen of the display unit 1 that spreads in front of the subject's eyes, as shown in FIG. 3. The shape and the color of the eye-target E is not particularly limited, but preferably, has a shape and a color which are easy for the subject to discriminate. As will be described later in detail, the eye-target showing part 2 controls the position and the movement of the eye-target E according to a judgment result of the judgment part 4.

The eye movement measuring part 3 measures the position and the movement of the subject's eyes by manipulating an image of the subject's eyes taken by the imaging device 30. The imaging device 30 comprises an infrared transmitting filter 31 and a CMOS sensor 32, and infrared radiation which was radiated from an infrared light LED 33 to an eye (eyeball) P of the subject is reflected by the eye P and the half mirror 11, and it comes into the CMOS sensor 32 through the filter 31, whereby the image of the subject's eye P can be taken. Because the infrared light LED 33 is disposed so as not to interfere with the field of view of the subject, and an emission wavelength of the infrared light LED 33 is in the infrared wavelength range, the light from the infrared light LED 33 is not detected by the subject, whereby it is possible to ease anxiety of the subject.

The judgment part 4 judges whether the subject can fixedly look at or follow the eye-target E based on the position and/or the movement of the eye-target shown on the display unit 1 by the eye-target showing part 2 and the position and/or the movement of the subject's eyes measured by the eye movement measuring part 3. Hereinafter, a judgment method will be described in detail.

Figure 4:
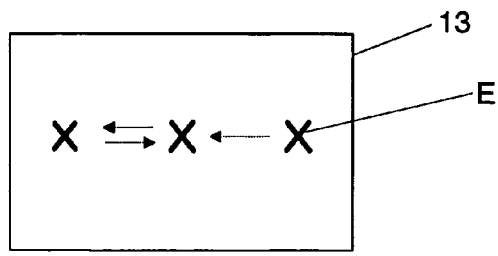
FIG. 4 is a view of one example of the eye-target to be shown to the subject in the cognitive function training unit.
Figure 5:
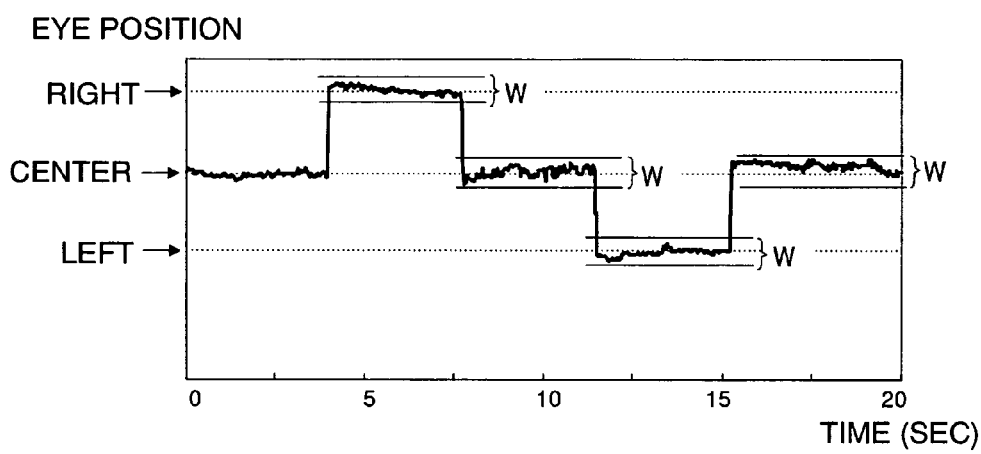
FIG. 5 is a view showing a change of an eye position of the subject at the time when the eye-target of FIG. 4 was shown to the subject.

For example, as shown in FIG. 4, the eye-target showing part 2 shows the eye-target E on the screen 13 of the display unit 1 from the right side of the screen to the center thereof, and then to the left side thereof, and then to the center, at a predetermined intervals (about 4 seconds), respectively (that is, the right side of the screen→the center→the left side→the center). The eye-target on the right side is at an angle of 30 degrees from the center to the right, and the eye-target on the left side is at an angle of 30 degrees from the center to the left. The subject is instructed to look at the center (cross-point) of the eye-target E. As shown in FIG. 5, when the subject is an able-bodied person, that is, when the subject does not have the cognitive dysfunction, the eye position of the subject moves from the right side to the center and then to the left side and then to the center (that is, the right side→the center→the left side→the center), together with the movement of the eye-target E. And, at each position, the eye position of the subject is within a predetermined variation range W. As above, when the eye position of the subject measured by the eye movement measuring part 3 is within a predetermined variation range when a stationary eye-target was shown to the subject, the judgment part 4 judges that the subject can fixedly look at the eye-target. On the other hand, if the subject has the cognitive dysfunction, such as the unilateral spatial neglect and so on, the eye position of the subject becomes unsteady in certain positions of the eye-target. So, when the eye position of the subject goes beyond the predetermined variation range when a stationary eye-target was shown to the subject, the judgment part 4 judges that the subject cannot fixedly look at the eye-target.

The size of the predetermined variation range W may be changed according to the position of the eye-target. For example, the variation range W may be enlarged at a position distant from the center in the horizontal direction, because it becomes difficult to fixedly look at the eye-target at such a position. Or, the variation range W may be changed according to an age of the subject. For example, the variation range W is enlarged as the age of the subject rises.

Figure 6:
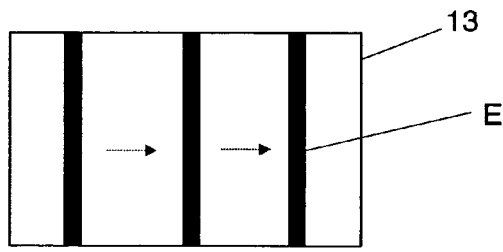
FIG. 6 is a view of one example of the eye-target to be shown to the subject in the cognitive function training unit.
Figure 7:
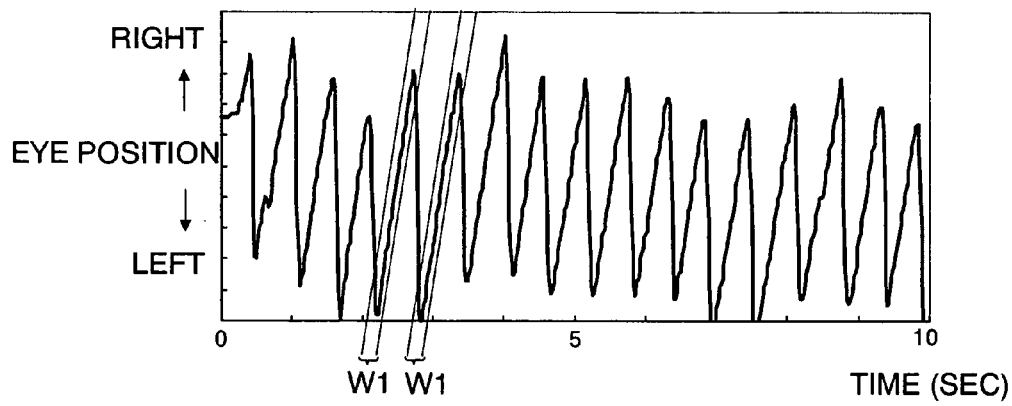
FIG. 7 is a view showing a change of the eye position of the subject at the time when the eye-target of FIG. 6 was shown to the subject.

By using the same principle, it is also possible to judge whether the subject can follow (chase) a moving eye-target. For example, as shown in FIG. 6, the eye-target showing part 2 repeatedly shows, on the screen 13, a vertically elongated eye-target E which appears on the left side of the screen and then moves to the right side. This eye-target is the eye-target that is generally used for an opticokinetic nystagmus test. The subject is instructed to pay attention to the center area of the screen and look at the eye-target E and transfer his or her gaze to the next eye-target that is around the center area when the eye-target E went out of the center area. As shown in FIG. 7, when the subject is an able-bodied person, the eye position of the subject moves from the left to the right and from the left to the right continuously and repeatedly, with the movement of the eye-target E. And, while the eye moves from the left to the right, that is while the subject follows the eye-target, the variation of the eye position is within a predetermined variation range W1 that has a certain gradient. As above, when the eye position of the subject is within a predetermined variation range having a certain gradient when a moving eye-target was shown to the subject, the judgment part 4 judges that the subject can follow the eye-target. On the other hand, if the eye position goes beyond the variation range W1, the judgment part 4 judges that the subject cannot follow the eye-target. The width of the variation range W1 may be changed according to the subject. Preferably, the gradient of the variation range W1 is set to a constant gradient when the movement speed of the eye-target is constant, and when the movement speed of the eye-target changes, the gradient is changed according to the change of the movement speed. As mentioned above, the judgment part 4 can judge whether the subject can fixedly look at or follow the eye-target based on the eye position of the subject.

The judgment result of the judgment part 4 is transmitted to the eye-target showing part 2. The eye-target showing part 2 can change the position and movement of the eye-target E at will by controlling, basically, any one of the position of the eye-target E, the movement speed, the amplitude, and the display time, or a combination thereof. For example, the eye-target showing part 2 can reciprocate the eye-target in the horizontal direction, or move the eye-target in a wave pattern, or blink the eye-target.

The eye-target that the eye-target showing part 2 shows on the screen is determined according to a training content of the subject. For example, when the subject is a patient of the unilateral spatial neglect having lowered cognitive faculty of the left side space, it is preferable to show an eye-target that can turn the patient's attention to the left side so as to gradually extend a space that the patient can recognize to the left side. So, when the subject is a patient of the unilateral spatial neglect, the eye-target showing part 2 shows the eye-target that appears on the left side of the screen and then moves to the right side, repeatedly, as shown in FIG. 6, for example. The velocity of the eye-target may be constant, or variable. When the velocity is variable, the velocity may be changed from a slow speed to a high speed, or conversely, may be changed from a high speed to a slow speed, or may be changed from a slow speed to a high speed and then to a slow speed again after it reached a maximum velocity. The subject is instructed to move his or her eyepoint to the left side as quickly as possible so as to look at the eye-target that appears from the left early. By repeating such training, it can be expected to extend the space that the subject can recognize to the left side gradually. Or, to the patient of the unilateral spatial neglect, an eye-target that moves from the right side to the left side may be shown repeatedly. In this case, the subject is instructed to follow (chase) the eye-target to the left side as far as possible. By this training too, it is expected to extend the space that the subject can recognize to the left side gradually.

It should be noted that, in order to conduct a drill for the cognitive dysfunction efficiently, it is important to grasp a symptom of the patient precisely and show an appropriate eye-target according to the symptom of the patient. If the training unit shows the eye-target without grasping the symptom of the patient, the eye-target may be shown in a space that the subject cannot recognize for a long time, or the eye-target may be shown only in a space that the subject can recognize, and therefore it is inefficient and it can inflict suffering on the patient.

Thus, the eye-target showing part 2 of the present invention changes the position and the movement of the eye-target according to the judgment result of the judgment part 4. For example, when the eye-target that appears on the left side of the screen and then moves to the right, as shown in FIG. 6, is shown to the subject of the unilateral spatial neglect, if the judgment means judges that the subject cannot follow the eye-target, the eye-target showing part 2 moves the position at which the eye-target appears to the right slightly so that the subject can follow the eye-target. Or, the eye-target showing part 2 may slow the movement speed of the eye-target. And, when the eye-target that moves from the right side of the screen to the left is shown to the subject of the unilateral spatial neglect, repeatedly, the eye-target showing part 2 returns the eye-target to the right side at the point of time when the judgment part 4 judges that the subject cannot follow the eye-target. As mentioned above, by changing the position and/or the movement of the eye-target so that the subject can fixedly look at or follow the eye-target when the judgment part 4 judges that the subject cannot fixedly look at or follow the eye-target, an appropriate eye-target can be shown according to the symptom of the patient, whereby it becomes possible to conduct a drill efficiently.

It is preferable that the amount of change of the position and/or the movement of the eye-target is changed according to severity of a disability of the subject. So, preferably, the judgment part 4 judges the severity of the subject according to a degree that the subject can not fixedly look at or follow the eye-target, and the eye-target showing part 2 changes the position and/or movement of the eye-target according to the severity. In this case, an appropriate eye-target can be shown according to the severity of a disability of the subject, whereby it becomes possible to conduct training more efficiently.

When a patient conducts training by using the cognitive function training unit constituted as above, he or she simply wears the unit on the head, and looks at the eye-target on the screen as instructed by an instructor. Or, training procedures may be displayed on the screen. Because this cognitive function training unit is a head-mount type, a large-scale equipment is not necessary, and therefore, it is possible to conduct training easily at any place. Furthermore, even if the subject moves his or her head, it is possible to show the eye-target at an intended position precisely because a coordinate system of the eye-target showing part 2 moves with the subject's head.

By the way, the cognitive dysfunction can not be cured rapidly, and it is cured gradually on a weekly or monthly basis. So, the cognitive function training unit may have a judgment mode for judging the severity of the subject and a rehabilitation mode for training the subject's cognitive function, and once the severity of the subject is judged in the judgment mode, the eye-target showing part 2 may show an eye-target pattern that was modified according to the degree of the severity in the rehabilitation mode.

In detail, in the judgment mode, the eye-target showing part 2 shows the eye-target in a predetermined test pattern (for example, the eye-target of FIG. 6) to the subject, and the judgment part 4 judges the severity of the subject according to the degree that the subject cannot fixedly look at or follow the eye-target. It is preferable that the severity includes a plurality of severity items, such as severity of a cognitive faculty in the horizontal direction, severity of a cognitive faculty in the vertical direction, and severity of a following faculty. In the rehabilitation mode, the eye-target showing part 2 modifies a position, a movement speed, a moving range, and so on of the eye-target in a predetermined patter (for example, the eye-target of FIG. 6) according to the severity of the subject that was judged in the judgment mode, and repeatedly shows an appropriate eye-target that corresponds to the severity of the subject, to the subject.

In this case, the subject measures his or her degree of severity in the judgment mode once a week or month, and in daily training, he or she conducts a drill in the rehabilitation mode by a program corresponding to the measured severity.

In the rehabilitation mode, it is not always necessary to use the head-mount type display because not the judgment but the training is a main purpose in the rehabilitation mode, so a generally-used display may be used. In this case, it is preferable to instruct a patient to follow the eye-target without moving his or her head as far as possible.

It is preferable that the eye-target showing part 2 can show an eye-target of a 3-dimensional image on the screen. As to a method for showing the 3-dimensional image, a well-known method, for example, a method that shows an independent image to the right and the left eyes, respectively, or a method that shows an image of odd number fields and an image of even number fields to the right and the left eyes, respectively, can be used. In this case, it becomes possible to show various eye-targets, for example, an eye-target that moves from a right back of the screen to a left front thereof, whereby it is possible to conduct training more efficiently according to the symptom of the subject.

Figure 8:
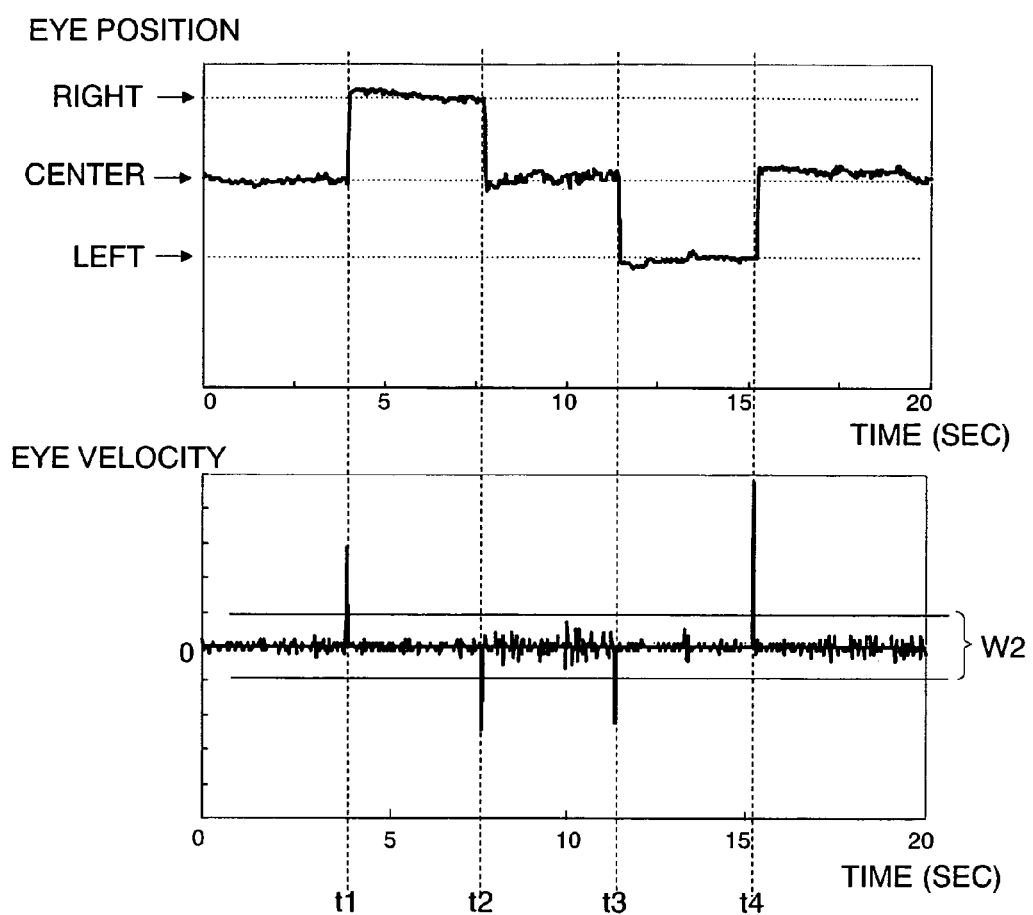
FIG. 8 is a view showing a change of an eye velocity of the subject calculated from the eye position at the time when the eye-target of FIG. 4 was shown to the subject.

Although, in this embodiment, the judgment part 4 judges whether the subject can fixedly look at or follow the eye-target by using the eye position of the subject, the judgment part 4 may judge whether the subject can fixedly look at or follow the eye-target by using an eye velocity of the subject. FIG. 8 shows an eye-position of the subject and the eye velocity of the subject calculated from the eye position at the time when the eye-target shown in FIG. 4 was shown. In FIG. 8, although a rapid eye movement, namely a saccade movement occurred at the points of time t1, t2, t3, and t4 at which the eye-target moved, the eye velocity is within a predetermined variation range W2, except for the saccade movement. As above, when the eye velocity of the subject measured by the eye movement measuring part 3 is within a predetermined variation range when a stationary eye-target was shown to the subject, the judgment part 4 can judge that the subject can fixedly look at the eye-target, and, when the eye velocity of the subject goes beyond the predetermined variation range when a stationary eye-target was shown to the subject, the judgment part 4 judges that the subject cannot fixedly look at the eye-target.

Figure 9:
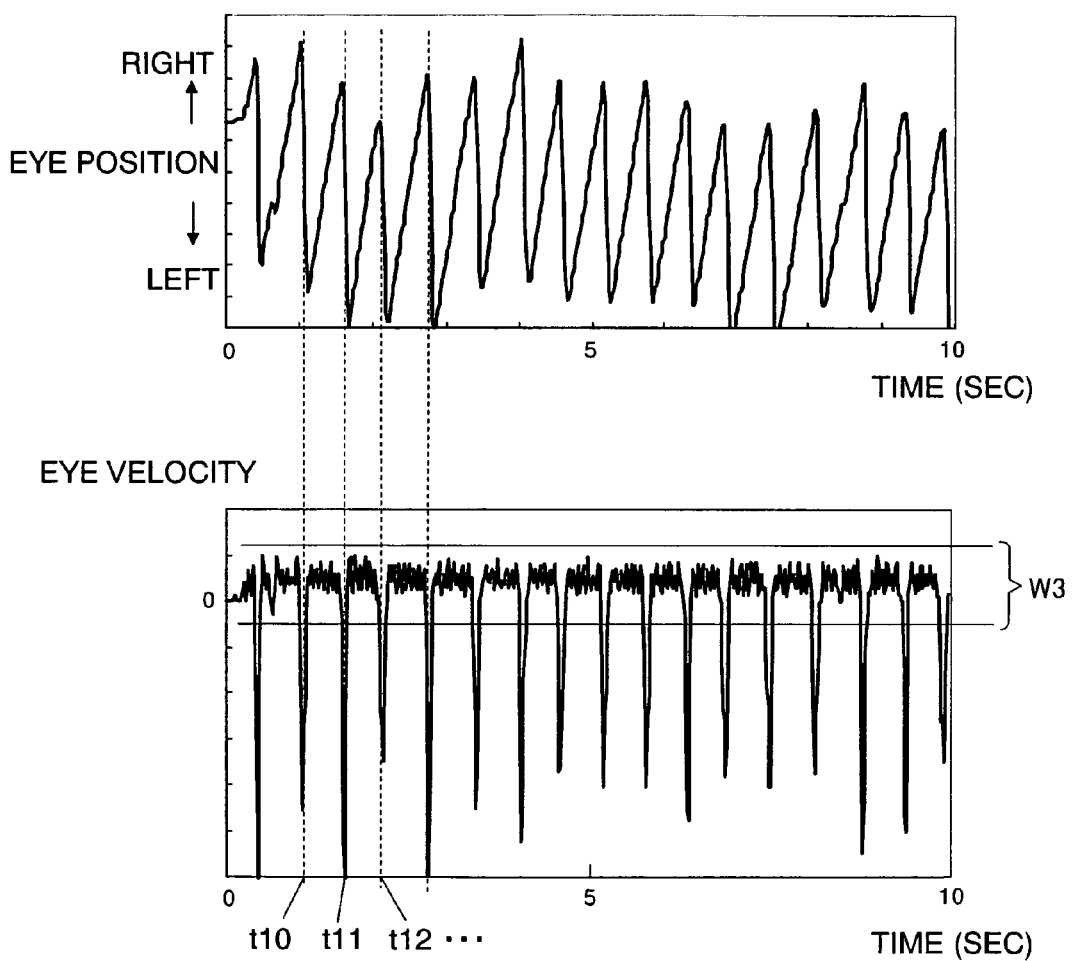
FIG. 9 is a view showing a change of an eye velocity of the subject calculated from the eye position at the time when the eye-target of FIG. 6 was shown to the subject.

In a similar way, FIG. 9 shows an eye-position of a subject and the eye velocity of the subject calculated from the eye position at the time when the eye-target shown in FIG. 6 was shown. In FIG. 9, although a rapid eye movement occurred at the points of time t10, t11, t12, . . . at which the eye moved from the right side to the left side, the eye velocity is within a predetermined variation range W3 while the eye moves from the left to the right, that is, while the subject follows the eye-target. As above, when the eye velocity of the subject is within a predetermined variation range when a moving eye-target was shown to the subject, the judgment part 4 judges that the subject can follow the eye-target, and, when the eye velocity of the subject goes beyond the predetermined variation range when a moving eye-target was shown to the subject, the judgment part 4 judges that the subject cannot follow the eye-target. In this case, too, the size of the variation ranges W2 and W3 may be changed according to the age of the subject or the velocity of the eye-target, and so on.

For reference, the reason why judgment part 4 can judge that the subject follows the eye-target when the eye-velocity is with the predetermined variation range W3 is that, generally, a continuous following movement of an eye (called a smooth eye movement) does not occur without an object that moves in a space continuously. That is, in a static visual space where an object does not move at all in a range of an eye field, it is impossible to make the following movement purposefully or voluntarily, and therefore the smooth continuous movement is not observed, and a discontinuous movement (called a saccade movement) always occurs. That is the case with not only an able-bodied person but also a patient of the unilateral spatial neglect, so the appearance of the continuous movement can constitute the basis of a fact that the subject follows the object accurately in an area called central retinal fovea which can see most minutely, that is, the subject looks at and follows the eye-target.

As mentioned above, it is possible to easily judge the appearance of the discontinuous movement because the discontinuous movement includes a precipitous component in the eye velocity as shown in FIG. 9.

In addition, by using the above mentioned fact, it is possible to do a calibration that checks the correlation between the eye position and the showing position of the eye-target beforehand. That is, because the appearance of the continuous movement of the eye can constitute the basis of the fact that the subject follows the object, it is possible to examine the correlation between the coordinate system of the eye measurement and the coordinate system of the showing position of the eye-target. By this, it is possible to increase reliability of the judgment means of the training unit of the present invention.

Figure 10:
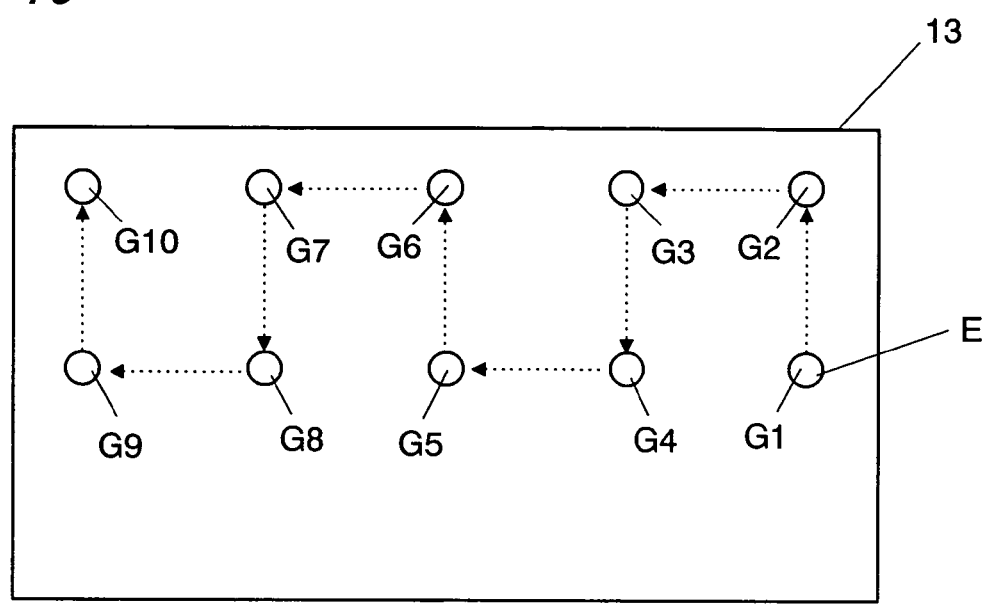
FIG. 10 is a view of one example of the eye-target to be shown to the subject in the cognitive function training unit.

Although, in this embodiment, the eye-target of FIG. 6 were taken as an example of the moving eye-target, the moving eye-target is not limited to the eye-target of FIG. 6, and an eye-target shown, for example, in FIG. 10 may be used. In FIG. 10, a circular eye-target E moves from the right end to the left end continuously via each point G1, G2, . . . , G9, and G10. In this case, too, the judgment part 4 judges that the subject follows the eye-target while the eye position or the eye velocity of the subject's eye is within a predetermined variation range.

Furthermore, it is possible to do the above mentioned calibration by using the eye-target of FIG. 10. For example, the subject is instructed to send a signal to the judgment part 4 by using an input means (not shown) when the circular figure comes to a predetermined position (there are at least two positions). The judgment part 4 monitors whether or not the subject follows the eye-target by the above mentioned method, and when it receives the signal from the subject while it judges that the subject follows the eye-target, it detects the eye position of the subject and the showing position of the eye-target shown by the eye-target showing part 2 at that time. Then, it calibrates the correlation between the coordinate system of the eye measurement and the coordinate system of the showing position of the eye-target by using the eye position and the showing position of the eye-target. As above, by doing the calibration when the judgment part judges that the subject follows the eye-target, it is possible to increase reliability of the calibration, whereby it is possible to increase the reliability of the judgment means.

As mentioned above, as many apparently widely different embodiments of this invention may be made without departing from the spirit and scope thereof, it is to be understood that the invention is not limited to the specific embodiments thereof except as defined in the appended claims.

The invention claimed is:

1. A cognitive function training unit for training cognitive function of a subject comprising:
   an eye-target showing means configured to show a movable eye-target on a display disposed in front of the subject's eye;
   an eye movement measuring means connected to an imaging device, the eye movement measuring means configured to measure at least one of a position and movement of the subject's eye by manipulating an image of the subject's eye obtained by said imaging device; and
   a judgment means configured to judge whether the subject can follow the eye-target based on at least one of a position and movement of the eye-target shown on said display and at least one of the position and the movement of the subject's eye measured by said eye movement measuring means,
   wherein said eye-target showing means is configured to show the eye-target repeatedly while changing at least one of the horizontal position, horizontal movement, amplitude and display time of the eye-target according to a judgment result of said judgment means, and
   wherein said judgment means is configured to judge that the subject cannot follow the eye-target when at least one of an eye position and an eye velocity of the subject measured by said eye movement measuring means is outside a predetermined variation range, and
   wherein said eye-target showing means is configured to change the position and/or the movement of the eye-target so that the subject can follow the eye-target, when said judgment means judges that the subject cannot follow the eye-target.

2. The cognitive function training unit as set forth in claim 1, wherein
   said eye-target showing means is configured to repeatedly show an eye-target which appears on a left side of a screen of said display and then moves to a right side,
   said eye-target showing means is configured to move a position at which the eye-target appears on the screen to the right when said judgment means judges that the subject can not follow the eye-target.

3. The cognitive function training unit as set forth in claim 1, wherein
   said eye-target showing means is configured to repeatedly show an eye-target which appears on a left side of a screen of said display and then moves to a right side,
   said eye-target showing means is configured to slow a movement speed of the eye-target when said judgment means judges that the subject cannot follow the eye-target.

4. The cognitive function training unit as set forth in claim 1, wherein
   said judgment means is configured to judge severity of the subject according to a degree that the subject cannot follow the eye-target,
   said eye-target showing means is configured to change the position and/or the movement of the eye-target according to the severity.

5. The cognitive function training unit as set forth in claim 4, wherein
   said cognitive function training unit has a judgment mode configured to judge the severity of the subject and a rehabilitation mode configured for training the cognitive function of the subject,
   in the judgment mode, said eye-target showing means being configured to show the eye-target in a predetermined test pattern and said judgment means being configured to judge the severity of the subject according to the degree that the subject cannot follow the eye-target,
   in the rehabilitation mode, said eye-target showing means being configured to change at last one of the position and the movement of the eye-target according to the severity of the subject judged in the judgment mode.

6. The cognitive function training unit as set forth in claim 1, wherein
   said eye-target showing means is configured to show an eye target of a 3-dimensional image on the display.

7. The cognitive function training unit as set forth in claim 1, wherein
   said display, said eye-target showing means, said eye movement measuring means, and said judgment means are housed in a case, said case being able to be mounted on a head of the subject.

8. The cognitive function training unit as set forth in claim 1, wherein
   said eye-target showing means is configured to repeatedly show an eye-target which appears on a right side of a screen of said display and then moves to a left side,
   said eye-target showing means is configured to move a position at which the eye-target appears on the screen to the left when said judgment means judges that the subject cannot follow the eye-target.

9. The cognitive function training unit as set forth in claim 1, wherein
   said eye-target showing means is configured to repeatedly show an eye-target which appears on a right side of a screen of said display and then moves to a left side,
   said eye-target showing means is configured to slow a movement speed of the eye-target when said judgment means judges that the subject cannot follow the eye-target.

10. A cognitive function training unit for training cognitive function of a subject comprising:
    an eye-target showing means configured to show a movable eye-target on a display disposed in front of the subject's eye;
    an eye movement measuring means connected to an imaging device, the eye movement measuring means configured to measure at least one of a position and movement of the subject's eye by manipulating an image of the subject's eye obtained by said imaging device; and
    a judgment means configured to judge whether the subject can perform at least one of:
    fixedly look at the eye-target based on at least one of the position and the movement of the eye-target shown on said display and at least one of the position and the movement of the subject's eye measured by said eye movement measuring means, and
    follow the eye-target based on at least one of the position and the movement of the eye-target shown on said display and at least one of the position and the movement of the subject's eye measured by said eye movement measuring means,
    wherein said eye-target showing means is configured to show the eye-target repeatedly while changing at least one of the position and the movement of the eye-target according to a judgment result of said judgment means,
    wherein said judgment means is configured to detect an eye position of the subject and a showing position of the eye-target, and calibrate a correlation between a coordinate system of the eye-movement measuring means and a coordinate system of the eye-target showing means based upon the detected eye-position and the showing position of the eye-target, and
    wherein said judgment means judges that the subject cannot follow the eye-target when at least one of an eye position and an eye velocity of the subject measured by said eye movement measuring means is outside a predetermined variation range.

* * * * *